US006235737B1

(12) United States Patent
Styczynski et al.

(10) Patent No.: US 6,235,737 B1
(45) Date of Patent: May 22, 2001

(54) REDUCTION OF HAIR GROWTH

(76) Inventors: Peter Styczynski, P.O. Box 387, Mt. Airy, MD (US) 21771; Gurpreet S. Ahluwalia, 7803 Turning Creek Ct., Potomac, MD (US) 20854

( * ) Notice: Subject to any disclaimer, the term of this patent is extended or adjusted under 35 U.S.C. 154(b) by 0 days.

(21) Appl. No.: 09/490,486

(22) Filed: Jan. 25, 2000

(51) Int. Cl.⁷ ..................... A61K 31/535; A61K 31/445; A61K 31/40; A61K 31/16

(52) U.S. Cl. ..................... 514/237.8; 514/315; 514/428; 514/628

(58) Field of Search ................... 514/237.8, 315, 514/428, 629

(56) References Cited

U.S. PATENT DOCUMENTS

| | | |
|---|---|---|
| 3,426,137 * | 2/1969 | Philpitt et al. . |
| 4,039,669 * | 8/1977 | Beylar et al. . |
| 4,139,638 * | 2/1979 | Neri et al. . |
| 4,161,540 * | 7/1979 | Neri et al. . |
| 4,191,775 * | 3/1980 | Glen . |
| 4,269,831 * | 5/1981 | Ferrari et al. . |
| 4,370,315 * | 1/1983 | Greff et al. . |
| 4,439,432 * | 3/1984 | Peat . |
| 4,508,714 * | 4/1985 | Cecic et al. . |
| 4,517,175 * | 5/1985 | Iwabuchi et al. . |
| 4,720,489 * | 1/1988 | Shander . |
| 4,885,289 * | 12/1989 | Breuer et al. . |
| 4,935,231 * | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Haverhagen . |
| 5,300,284 | 4/1994 | Wiechers et al. . |
| 5,328,686 | 7/1994 | Shander et al. . |
| 5,362,748 | 11/1994 | Schwen et al. . |
| 5,364,885 | 11/1994 | Ahluwalia et al. . |
| 5,411,991 | 5/1995 | Shander et al. . |
| 5,444,090 | 8/1995 | Ahluwalia et al. . |
| 5,455,234 | 10/1995 | Ahluwalia et al. . |
| 5,468,476 | 11/1995 | Ahluwalia et al. . |
| 5,474,763 | 12/1995 | Shander et al. . |
| 5,554,608 | 9/1996 | Ahluwalia et al. . |
| 5,645,825 | 7/1997 | Hillebrand et al. . |
| 5,648,394 | 7/1997 | Boxall et al. . |
| 5,652,273 | 7/1997 | Henry et al. . |
| 5,674,477 | 10/1997 | Ahluwalia . |
| 5,728,736 | 3/1998 | Shander et al. . |
| 5,776,442 | 7/1998 | Ahluwalia . |
| 5,824,665 | 10/1998 | Henry et al. . |
| 5,840,752 | 11/1998 | Henry et al. . |
| 5,908,867 | 6/1999 | Henry et al. . |
| 5,939,458 | 8/1999 | Henry et al. . |
| 5,958,946 | 9/1999 | Styczynski et al. . |
| 5,962,466 | 10/1999 | Styczynski et al. . |
| 6,020,006 | 2/2000 | Styczynski et al. . |
| 6,037,326 | 3/2000 | Styczynski et al. . |

FOREIGN PATENT DOCUMENTS

| | | | |
|---|---|---|---|
| 0 413 528 A1 | * | 2/1991 | (EP) . |
| 0 532 219 A2 | * | 3/1993 | (EP) . |
| 1 458 349 | * | 12/1976 | (GB) . |
| WO 98/02134 | * | 1/1998 | (WO) . |

OTHER PUBLICATIONS

Lee et al., "Improved Inhibitors of Glucosylceramide Synthase", J. Biol. Chem., vol. 274, pp. 14662–669, May 21, 1999.*

Botchkarev et al., "A New Role for Neurotrophin–3 Involvement in the Regulation of Hair Follicle Regression (Catagen)" American Journal of Pathology, vol. 153, No. 3, Sep. 1998.*

Botchkarev et al., "Neurotrophin–3 Involvement in the Regulation of Hair Follicle Morphogenesis", The Journal of Investigative Dermatology, vol. 111, No. 2, Aug. 1998.*

Ichikawa et al., "Glucosylceramine synthase and glycosphingolipid synthesis", trends in Cell Biology, pp. 198–202, May 1998.

Hoffman et al., "Interleukin–1–β–Induced Inhibition of Hair Growth in Vitro is Mediated by Cyclic AMP", The Journal of Investigative Dermatology, vol. 108, pp. 40–42, 1997.

Bielawska et al., "(1S,2R)–D–erythro–2–(N–Myrisoylamino)–1–phenyl–1–propanol as an Inhibitor of Ceramidase", The Journal of Biological Chemistry, vol. 271, pp. 12646–54, May 24, 1996.

Rani et al., "Cell Cycle Arrest Induced by an Inhibitor of Glucosylceramide Synthase", The American Society for Biochemistry and Molecular Biology, Inc., vol. 270, pp. 2859–67, Feb. 10, 1995.

Platt et al., "N–Butyldeoxynojirimycin Is a Novel Inhibitor of Glycolipid Biosynthesis", The Journal of Biological Chemistry, vol. 269, pp. 8362–65, Mar. 18, 1994.

Andrew G. Messenger, "The Control of Hair Growth: An Overview", Journal for Investigative Dermatology, Inc., 1993.

Weinberg et al., "Reconstitution of Hair Follicle Development in Vivo: Determination of Follicle Formation, Hair Growth, and Hair Quality by Dermal Cells", The J. of Invest. Dermatology, vol. 100, No. 3, Mar. 1993.

Matsuo et al., "A rapid and simple assay method for UDP–glucose:ceramide glucosyltransferase", Biochemicsa et Biophysica Acta, pp. 97–103 (1992).

Ebling et al., "The Biology of Hair", Dermatologic Clinics, vol. 5, pp. 467–481, Jul. 1987.

Hattori et al., "Biochemical Analysis of Hair Growth from the Aspects of Aging and Enzyme Activities", The Journal of Dermatology, vol. 10, 1983.

Yoshio Sato, "Hair Cycle and Its Control Mechanism", Biology and Disease of Hair, pp. 3–13, 1975.

Styczynski et al., "Reduction of Hair Growth", U.S. Serial No. 09/010,227, filed Jan. 21, 1998.

* cited by examiner

*Primary Examiner*—Rebecca Cook
(74) *Attorney, Agent, or Firm*—Fish & Richardson P.C.

(57) ABSTRACT

Mammalian hair growth is reduced by applying to the skin a composition that increases cellular ceramide levels.

43 Claims, No Drawings

REDUCTION OF HAIR GROWTH

BACKGROUND OF THE INVENTION

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

Ceramide is a naturally occurring sphingolipid metabolite present in skin and other tissues both intra- and extracellularly. Biosynthesis of ceramide in cells generally starts by the condensation of the amino acid serine and palmitoyl-CoA resulting in the formation of 3-ketodihydrosphingosine, which is subsequently reduced to dihydrosphingosine. The amide linkage of fatty acyl groups to dihydrosphingosine forms dihydroceramide. The dihydroceramide is converted to ceramide by the introduction of a trans-4,5-double bond. Once formed, ceramide acts as a precursor for the synthesis of other complex sphingolipids such as galactosylceramide, glucosylceramide, and acyl ceramide. Most glycosphingolipids are synthesized from ceramide via glucosylceramide, the formation of which is catalyzed by glucosylceramide synthase.

Ceramide is also formed in cells by pathways of complex glycosphingolipid catabolism. For example, the breakdown of sphingomyelin through the action of sphingomyelinases results in the formation of ceramide. Another set of enzymes that may regulate cellular ceramide levels are ceramidases, which break down ceramide to sphingosine.

SUMMARY OF THE INVENTION

The invention features reducing unwanted mammalian (including human) hair growth—particularly androgen-stimulated hair growth—by increasing cellular ceramide levels. Cellular ceramide levels may be increased, for example, by applying to the skin a composition including (1) an inhibitor of glucosylceramide synthase, (2) an inhibitor of ceramidase; (3) ceramide (N-acyl-trans-D-erythro-2-amino-4-octadecene-1,3-diol); (4) a ceramide analog; and/or (5) an inducer of spingomylinase. A ceramide analog is a chemical derivative of the ceramide molecule that either behaves as ceramide or is degraded in cells to ceramide. The unwanted hair growth which is reduced may be normal hair growth, or hair growth that results from an abnormal or diseased condition. For purposes of this application, glucosylceramide synthase includes glucosyl ceramide transferase.

Other features and advantages of the invention may be apparent from the description of the preferred embodiments thereof, and from the claims.

DESCRIPTION OF THE EMBODIMENTS

A preferred composition includes at least one compound that increases cellular ceramide levels when applied topically in a cosmetically and/or dermatologically acceptable vehicle. The composition may be a solid, semi-solid, or liquid. The composition may be, for example, a cosmetic and dermatologic product in the form of an, for example, ointment, lotion, foam, cream, gel, or hydroalcoholic solution. The composition may also be in the form of a shaving preparation or an aftershave. The vehicle itself can be inert or it can possess cosmetic, physiological and/or pharmaceutical benefits of its own.

Examples of inhibitors of glucosylceramide synthase: 1-phenyl-2-decanoylamino-3-morpholino-1-propanol (PDMP); 1-phenyl-2-hexadecanoylamino-3-morpholino-1-propanol (PPMP); 1-phenyl-2-hexadecanoylamino-3-pyrrolidino-1-propanol (PPPP); 1-phenyl-2-palmitoylamino-3-pyrrolidino-1-propanol (P4); D-threo-4'-hydroxy-P4; D-threo-3',4'-methylenedioxyphenyl-P4; D-threo-trimethylenedioxyphenyl-P4; D-threo-3',4'-ethylenedioxyphenyl-P4; N-butyldeoxynojirimycin (NBDN); and N-(5-adamantane)-1-yl-methoxy)pentyl)-deoxy norjirimycin. See Rani et al., J. Biol. Chem. 270: 2859–2867, 1995; Olshefski and Ladisch, J. Neurochem. 70: 467–472, 1998; Lee et al., J. Biol. Chem. 274: 14662–14669, 1999; Neises et al., Biol. Cell 89: 123–131, 1997; and Platt et al. J. Biol Chem. 269: 8362–8365, 1994.

Examples of inhibitors of ceramidase include the following: D-erythro-2-(N-myristoylamino)-1-phenyl-1-propanol (D-erythro-MAPP); N-oleoyl ethanolamine; and (1S,2R)-(+)-phenylpropanolamine. See Spinedi et al., Biochem. Biophys. Res. Commun. 255: 456–459, 1999; Bielawska et al., J. Biol. Chem. 271: 12646–12654, 1996.

Examples of ceramide analogs include the following: N-acetylsphingosine (C2-ceramide); N-hexanoylsphingosine (C6-ceramide); N-octanoylsphingosine (C8-ceramide); N-octanoyl-DL-erythro dihydrosphingosine; N-octyl-D-erythro-sphingosine; and N-thioacetylsphingosine; and 4-dodecanoylamino-decan-5-ol. See Park et al., Exp. Mol. Med. 31: 142–150, 1999; Irie and Hirabayashi, J. Neurosci. Res., 54: 475–485, 1998; Karasavvas et al., Eur. J. Biochem. 236: 729–737, 1996; and Bektas et al., Exp. Dermatol. 7: 342–249, 1998.

The composition may include more than one compound that increases cellular ceramide levels. In addition, the composition may include one or more other types of hair growth reducing agents, such as those described in U.S. Pat. Nos. 4,885,289; 4,720,489; 5,132,293; 5,096,911; 5,095,007; 5,143,925; 5,328,686; 5,440,090; 5,364,885; 5,411,991; 5,648,394; 5,468,476; 5,475,763; 5,554,608; 5,674,477; 5,728,736; 5,652,273; WO 94/27586; WO 94/27563; and WO 98/03149, all of which are incorporated herein by reference.

The concentration of the compound that increases cellular ceramide levels in the composition may be varied over a wide range up to a saturated solution, preferably from 0.1% to 30% by weight or even more; the reduction of hair growth increases as the amount of compound applied increases per unit area of skin. The maximum amount effectively applied is limited only by the rate at which the compound penetrates the skin. The effective amounts may range, for example, from 10 to 3000 micrograms or more per square centimeter of skin.

Vehicles can be formulated with liquid or solid emollients, solvents, thickeners, humectants and/or powders. Emollients include stearyl alcohol, mink oil, cetyl alcohol, oleyl alcohol, isopropyl laurate, polyethylene glycol, olive oil, petroleum jelly, palmitic acid, oleic acid, and myristyl myristate. Solvents may include ethyl alcohol, isopropanol, acetone, diethylene glycol, ethylene glycol, dimethyl sulfoxide, and dimethyl formamide.

The composition also may include components that enhance the penetration of the compound into the skin and/or to the site of action. Examples of penetration enhancers include urea, polyoxyethylene ethers (e.g., Brij-30 and Laureth-4), 3-hydroxy-3,7,11-trimethyl-1,6,10-dodecatriene, terpenes, cis-fatty acids (e.g., oleic acid, palmitoleic acid), acetone, laurocapram, dimethylsulfoxide, 2-pyrrolidone, oleyl alcohol, glyceryl-3-stearate, propan-2-ol, myristic acid isopropyl ester, and propylene glycol.

The composition also can be formulated to provide a reservoir within or on the surface of the skin to provide for a continual slow release of a compound that increases cellular ceramide levels. The composition also may be formulated to evaporate slowly from the skin, allowing the inhibitor extra time to penetrate the skin.

The following are examples of compositions including a compound that increases cellular ceramide levels.

EXAMPLE 1

Compositions were prepared containing PDMP, PPMP, PPPP, (1S,2R)-(+)-phenylpropanolamine and N-oleoylethanolamine in a vehicle containing water 68%, ethanol 16%, propylene glycol 5%, dipropylene glycol 5%, benzyl alcohol 4%, and propylene carbonate 2%. These compositions were tested for their effect on hair growth; the results are provided in Table 1, along with the weight quantities of the relevant compound in the composition.

EXAMPLE 2

Compositions were prepared containing C8-ceramide, C6-ceramide and C2-ceramide in a vehicle containing water 68%, ethanol 16%, propylene glycol 5%, dipropylene glycol 5%, benzyl alcohol 4%, and propylene carbonate 2%. The compositions were tested for their effect on hair growth; the results are provided in Table 1, along with the weight quantities of the relevant compound in the composition.

EXAMPLE 3

Compositions were prepared including the compounds listed in Example 1 (same weight quantities) in a vehicle containing water 80.84%, glyceryl stearate 4.24%, polyethylene glycol 100-stearate 4.09%, cetearyl alcohol 3.05%, ceteareth-20 2.5%, mineral oil 2.22%, stearyl alcohol 1.67%, and dimethicone 0.56%.

EXAMPLE 4

Compositions were prepared including the compounds listed in Example 2 (same weight quantities) in a vehicle containing water 80.84%, glyceryl stearate 4.24%, polyethylene glycol 100-stearate 4.09%, cetearyl alcohol 3.05%, ceteareth-20 2.5%, mineral oil 2.22%, stearyl alcohol 1.67%, and dimethicone 0.56%.

Optionally, one of the penetration enhancers mentioned previously may be added to a composition. A penetration enhancer could be added at concentrations of, for example, 0.10% to 20% by weight. The preferred concentration is 0.5% to 5% by weight.

The composition should be topically applied to a selected area of the body from which it is desired to reduce hair growth. For example, the composition can be applied to the face, particularly to the beard area of the face, i.e., the cheek, neck, upper lip, and chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women suffering from hirsutism or other conditions. In humans, the composition should be applied once or twice a day, or even more frequently, to achieve a perceived reduction in hair growth. Perception of reduced hair growth could occur as early as 24 hours or 48 hours (for instance, between normal shaving intervals) following use or could take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced.

Golden Syrian Hamster Assay

Male intact Golden Syrian hamsters are considered acceptable models for human beard hair growth in that they display oval shaped flank organs, one on each side, each about 8 mm. in major diameter. These organs produce fine light colored hair typical of the animal pelage found on the body. In response to androgens the flank organs produce dark coarse hair similar to male human beard hair. To evaluate the effectiveness of a composition including a compound that increases cellular ceramide levels, the flank organs of each of a group of hamsters are depilated by applying a thioglycolate based chemical depilatory (Surgex) and/or shaved. To one organ of each animal 10 $\mu$l. of vehicle alone once a day is applied, while to the other organ of each animal an equal amount of vehicle containing a compound that increases cellular ceramide levels is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 15%, more preferably at least about 25%, and most preferably at least about 35% when tested in the Golden Syrian hamster assay. Compositions described in examples 1 and 2 (above)

were tested in the Golden Syrian hamster assay; the results are provided in Table 1:

TABLE 1

Reduction of Hair Mass

| Compound | Weight % | % Reduction | Left (mg) | Right (mg) |
|---|---|---|---|---|
| PDMP | 10 | 40 ± 11 | 0.99 ± .11 | 1.83 ± .20 |
| PPMP | 2.5 | 32 ± 14 | 1.60 ± .44 | 2.37 ± .66 |
| PPPP | 1 | 42 ± 13 | 0.95 ± .31 | 1.80 ± .49 |
| (1S,2R)-(+)-Phenyl propanolamine | 10 | 40 ± 6 | 1.72 ± .27 | 2.96 ± .46 |
| N-Oleoylethanolamine | 10 | 48 ± 6 | 1.00 ± .11 | 1.99 ± .16 |
| $C_8$-Ceramide | 1 | 17 ± 12 | 1.18 ± .17 | 1.49 ± .12 |
| $C_8$-Ceramide | 3 | 30 ± 5 | 1.53 ± .16 | 2.23 ± .28 |
| $C_6$-Ceramide | 2.5 | 40 ± 7 | 1.99 ± .39 | 3.17 ± .39 |
| $C_2$-Ceramide | 1 | 16 ± 7 | 1.67 ± .18 | 2.14 ± .33 |
| $C_2$-Ceramide | 3 | 42 ± 7 | 1.85 ± .34 | 3.10 ± .36 |

Glucosylceramide Transferase Assay

This assay has been previously described generally by Matsuo et al., Bochimica et Biophysica Acta, 1116:97–103, 1992. The assay measures the transfer of glucose from $^3$H-UDP-glucose to ceramide-silica-60 substrate in the presence of flank organ-derived, hair follicle tissue homogenates. The solid ceramide substrate was prepared by dissolving ceramide in chloroform and adding silica-60 to give a concentration of 20 mg ceramide/mg silica. The chloroform was evaporated under N2 gas and the silica-ceramide was allowed to dry completely before use in the assay. Each reaction mixture in the assay contained 10 mg of the solid ceramide substrate, 50 µl of hair follicle extract from hamster flank organ, 100 µl $^3$H-UDP-glucose (0.54 mM), 250 µl MOPS buffer (25 mM, pH 6.5) containing 1 mM $MgCl_2$, 2 mM MnCl2, 0.5 mM NADH, and either 600 µl $H_2O$ or 600 µl $H_2O$ containing a compound that is an inhibitor of glucosylceramide transferase. Reactions were initiated with the addition of the radiolabeled glucose and incubated at 37° C. with gentle rocking. Background was determined using silica-60 without ceramide. Reaction mixtures were microcentrifuged and the silica-ceramide was washed 3 times with 1 ml phosphate buffer saline (PBS) and analyzed using liquid scintillation.

The assay conditions were optimized for time, protein concentration and ceramide substrate concentration. The catalytic activity of the enzyme was found to be linear with time over a 20 minute incubation period at 37° C. Linearity with respect to protein concentration was shown to range from 10 micrograms/mL up to 75 micrograms/mL. Also, glucosylceramide synthase activity was linear with respect to ceramide substrate concentration in the range from 5 µg/mL up through 50 µg/mL with enzyme activity ranging from 625–850 pmoles/minute×mg protein.

The hair follicle extracts were found to possess glucosylceramide synthase activity. Several known inhibitors of glucosylceramide synthase (PDMP, PPMP and PPPP) that were demonstrated to reduce hair mass were also shown to inhibit flank organ-derived hair follicle glucosylceramide synthase activity, in vitro (Table 2). In general, the enzyme inhibition is dependent on the concentration of the inhibitor used, such that increasing the inhibitor dose results in increased inhibition of the enzyme.

TABLE 2

Inhibition of hair follicle glucosylceramide synthase activity (pmoles $^3$H-glucose incorporated/min × mg protein)

| Inhibitor | Control Activity Without Inhibitor | Avtivity with Inhibitor Present | Percent Inhibition |
|---|---|---|---|
| PDMP 0.5 mM | 177 ± 15 | 15 ± 10 | 92 ± 6 |
| PPMP 0.5 mM | 173 ± 15 | 46 ± 11 | 73 ± 6 |
| PPPP 0.5 mM | 190 ± 16 | 149 ± 31 | 22 ± 9 |

Generally, preferred inhibitors of glucosylceramide synthase inhibited hair follicle glucosylceramide synthase activity by at least 20% and preferably by 50% when tested in the assay described above using the 0.5 mM concentration of the inhibitor used to generate the test results in Table 2.

An analagous assay can also be used to test inhibitors of ceramidase for their inhibiting affect on hair follicle ceramidase activity.

Ceramidase activity can be measured by incubating 40 mM of a buffer containing 0.21 M sucrose, 0.8 mM EDTA, 4 mg/ml deoxycholate, 0.7 mg/ml Triton X-100, 0.62 mM [$^3$H] ceramide and 0.1–0.5 mg protein. The compound to be tested for ceramidase inhibition can be added at 0.5 mM. Reactions are then incubated at 37° C. for 60 minutes and the reactions are stopped by the additions of 100 µl palmitic acid and 4 ml 10% citric acid and 5 ml hexane. The tubes are mixed and centrifuged and the hexane phase transferred to a clean tube and the aqueous phase re-extracted with an additional 5 ml hexane. The hexane extracts are combined and dried under nitrogen. The residue is dissolved in 100 µl chloroform and a 4 µl aliquot is removed for analysis by liquid scintillation. A 16 µl aliquot is applied to a lane on a thin layer plate, which is then developed with hexane; ethyl ether; acetic acid (70:30:1). The release of free fatty acid is determined by radiochemical analysis to indicate ceramidase activity. See generally, Wertz, P. W. and Downing, D., "Ceramidase activity in porcine epidermis", FEBS 268 (1):110–112, 1990. Generally, preferred inhibitors of ceramidase would inhibit hair follicle ceramidase activity by at least 20% and preferably at least 50% when tested in the above assay.

Other embodiments are within the claims.

What is claimed is:

1. A method of reducing mammalian hair growth which comprises selecting an area of skin from which reduced hair growth is desired; and applying to said area of skin a dermatologically acceptable composition comprising a compound that increases cellular ceramide levels in an amount effective to reduce hair growth.

2. The method of claim 1, wherein the concentration of said compound in said composition is between 0.1% and 30%.

3. The method of claim 1, wherein the compound provides a reduction in hair growth of at least 15% when tested in the Golden Syrian Hamster assay.

4. The method of claim 1, wherein the compound provides a reduction in hair growth of at least 25% when tested in the Golden Syrian Hamster assay.

5. The method of claim 1, wherein the compound is applied to the skin in an amount of from 10 to 3000 micrograms of said compound per square centimeter of skin.

6. The method of claim 1, wherein said mammal is a human.

7. The method of claim 6, wherein said area of skin is on the face of the human.

8. The method of claim 6, wherein the composition is applied to the area of skin in conjunction with shaving.

9. The method of claim 6, wherein said area of skin is on a leg of the human.

10. The method of claim 6, wherein said area of skin is on an arm of the human.

11. The method of claim 6, wherein said area of skin is in an armpit of the human.

12. The method of claim 6, wherein said area of skin in on the torso of the human.

13. The method of claim 1, wherein the composition is applied to an area of skin of a woman suffering from hirsutism.

14. The method of claim 1, wherein said hair growth comprises androgen stimulated hair growth.

15. The method of claim 1, wherein the composition further comprises a second compound that also causes a reduction in hair growth.

16. A method of reducing mammalian hair growth, which comprises selecting an area of skin from which reduced hair growth is desired; and applying to said area of skin a dermatologically acceptable composition comprising an inhibitor of glucosylceramide synthase in an amount effective to reduce hair growth.

17. The method of claim 16, wherein the inhibitor is 1-phenyl-2-decanoylamino-3-morpholino-1-propanol.

18. The method of claim 16, wherein the inhibitor is 1-phenyl-2-hexadecanoylamino-3-morpholino-1-propanol.

19. The method of claim 16, wherein the inhibitor is 1-phenyl-2-hexadecanoylamino-3-pyrrolidino-1-propanol.

20. The method of claim 16, wherein the inhibitor is 1-phenyl-2-palmitoylamino-3-pyrrolidino-1-propanol.

21. The method of claim 16, wherein the inhibitor is D-threo-4'-hydroxy-1-phenyl-2-palmitoylamino-3-pyrrolidino-1-propanol.

22. The method of claim 16, wherein the inhibitor is D-threo-3',4'-methylenedioxyphenyl 1-phenyl-2-palmitoylamino-3-pyrrolidino-1-propanol.

23. The method of claim 16, wherein the inhibitor is D-threo-trimethylenedioxyphenyl 1-phenyl-2-palmitoylamino-3-pyrrolidino-1-propanol.

24. The method of claim 16, wherein the inhibitor is D-threo-3',4'-methylenedioxyphenyl 1-phenyl-2-palmitoylamino-3-pyrrolidino-1-propanol.

25. The method of claim 16, wherein the inhibitor is N-butyldeoxynojirimycin (NBDN).

26. The method of claim 16, wherein the inhibitor is N-(5-adamantane)-1-yl-methoyx)pentyl)-deoxy norjirimycin.

27. The method of claim 16, wherein the inhibitor inhibits glucosylceramide synthase activity in hair follicles by at least 20%.

28. The method of claim 16, wherein the inhibitor inhibits glucosylceramide synthase activity in hair follicles by at least 50%.

29. A method of reducing mammalian hair growth, which comprises selecting an area of skin from which reduced hair growth is desired; and applying to said area of skin a dermatologically acceptable composition comprising an inhibitor of ceramidase in an amount effective to reduce hair growth.

30. The method of claim 29, wherein the inhibitor is D-erythro-2-(N-myristoylamino)-1-phenyl-1-propanol.

31. The method of claim 29, wherein the inhibitor is N-oleyl ethanolamine.

32. The method of claim 29, wherein the inhibitor is (1S,2R)-(+)-phenylpropanolamine.

33. A method of reducing mammalian hair growth, which comprises selecting an area of skin from which reduced hair growth is desired; and applying to said area of skin a dermatologically acceptable composition comprising ceramide or a ceramide analog.

34. The method of claim 33, wherein the composition comprises ceramide.

35. The method of claim 33, wherein the composition comprises N-hexanoylsphingosine.

36. The method of claim 33, wherein the composition comprises N-octanoylsphingosine.

37. The method of claim 33, wherein the composition comprises N-octanoyl-DL-erythro dihydrosphingosine.

38. The method of claim 33, wherein the composition comprises N-octyl-D-erythro-sphingosine.

39. The method of claim 33, wherein the composition comprises N-thioacetylsphingosine.

40. The method of claim 33, wherein the composition comprises 4-dodecanoylamino-decan-5-ol.

41. The method of claim 33, wherein the inhibitor inhibits ceramidase activity in hair follicles by at least 20%.

42. The method of claim 33, wherein the inhibitor inhibits ceramidase activity in hair follicles by at least 50%.

43. A method of reducing mammalian hair growth, which comprises selecting an area of skin from which reduced hair growth is desired; and applying to said area of skin a dermatologically acceptable composition comprising an inducer of sphingomylinase in an amount effective to reduce hair growth.

* * * * *